United States Patent
Jin

(10) Patent No.: US 10,994,018 B2
(45) Date of Patent: May 4, 2021

(54) LONG-ACTING PALMITIC ACID-CONJUGATED GNRH DERIVATIVE, AND PHARMACEUTICAL COMPOSITION CONTAINING SAME

(71) Applicant: NOVEL PHARMA INC., Seoul (KR)

(72) Inventor: Dong Kyu Jin, Seoul (KR)

(73) Assignee: NOVEL PHARMA INC., Seoul (KR)

( * ) Notice: Subject to any disclaimer, the term of this patent is extended or adjusted under 35 U.S.C. 154(b) by 0 days.

(21) Appl. No.: 16/630,704

(22) PCT Filed: Jun. 20, 2018

(86) PCT No.: PCT/KR2018/006954
§ 371 (c)(1),
(2) Date: Jan. 13, 2020

(87) PCT Pub. No.: WO2019/066199
PCT Pub. Date: Apr. 4, 2019

(65) Prior Publication Data
US 2020/0268896 A1    Aug. 27, 2020

(30) Foreign Application Priority Data
Sep. 27, 2017 (KR) .................. 10-2017-0125291

(51) Int. Cl.
*A61K 47/64* (2017.01)
*A61K 47/54* (2017.01)
*A61K 38/09* (2006.01)

(52) U.S. Cl.
CPC .............. *A61K 47/64* (2017.08); *A61K 38/09* (2013.01); *A61K 47/542* (2017.08)

(58) Field of Classification Search
None
See application file for complete search history.

(56) References Cited

U.S. PATENT DOCUMENTS

| | | | |
|---|---|---|---|
| 6,015,789 A | 1/2000 | Suzuki et al. | |
| 8,722,078 B2 | 5/2014 | Gibson et al. | |
| 9,150,615 B2 | 10/2015 | Hsiao et al. | |
| 9,694,051 B2 | 7/2017 | Hsu et al. | |
| 2005/0282731 A1 | 12/2005 | Bauer et al. | |
| 2008/0027003 A1* | 1/2008 | Burov | C07K 7/23 514/130 |
| 2013/0060004 A1 | 3/2013 | Kuppanna et al. | |
| 2014/0155329 A1* | 6/2014 | Hsu | A61P 9/02 514/15.6 |
| 2015/0148295 A1* | 5/2015 | Burton | A61P 19/10 514/11.9 |
| 2015/0265535 A1 | 9/2015 | Yu et al. | |
| 2015/0297726 A1 | 10/2015 | Yoon et al. | |

FOREIGN PATENT DOCUMENTS

| | | |
|---|---|---|
| CN | 105797134 A | 7/2016 |
| JP | 10-45625 A | 2/1998 |
| KR | 10-2005-0084829 A | 8/2005 |
| KR | 10-2014-0027232 A | 3/2014 |
| KR | 10-2014-0086722 A | 7/2014 |
| KR | 10-2014-0086741 A | 7/2014 |
| RU | 2271826 C2 | 3/2006 |
| RU | 2325160 C1 | 5/2008 |
| WO | 2010025435 A2 | 3/2010 |
| WO | 2015/014653 A1 | 2/2015 |

OTHER PUBLICATIONS

Pratap Kumar, et al., "Gonadotropin-releasing hormone analogs: Understanding advantages and limitations", Journal of Human Reproductive Sciences, Jul.-Sep. 2014, pp. 170-174, vol. 7, No. 3.
Peter A. Lee, et al., "36-Month Treatment Experience of Two Doses of Leuprolide Acetate 3-Month Depot for Children With Central Precocious Puberty", J Clin Endocrinol Metab, Sep. 2014, pp. 3153-3159, vol. 99, No. 9.
Cuilian Peng, et al., "Determination of physicochemical properties and degradation kinetics of triamcinolone acetonide palmitate in vitro", Drug Development and Industrial Pharmacy, 2010, 4 pages, vol. 36, Iss. 12.
Korean Office Action for Application No. 10-2018-0070866 dated Nov. 8, 2019.
International Search Report for PCT/KR2018/006954 dated Nov. 2, 2018 [PCT/ISA/210].
Communication dated Aug. 19, 2020 from the China National Intellectual Property Administration in Application No. 201880058702.1.
Communication dated Oct. 16, 2020, from the Russian Patent Office in Application No. 2020109232/10.
Seung Ho Choi et al., "Hydrophobic ion pair formation between leuprolide and sodium oleate for sustained release from biodegradable polymeric microspheres", International Journal of Pharmaceutics, vol. 203, 2000, pp. 193-202.
Michael J. Hackett et al. "Fatty acids as therapeutic auxiliaries for oral and parenteral formulations", Advanced Drug Delivery Reviews, vol. 65, 2013, pp. 1331-1339 (9 pages total).
Communication dated Feb. 8, 2021, from the European Patent Office in application No. 18862614.7.

* cited by examiner

*Primary Examiner* — Lianko G Garyu
(74) *Attorney, Agent, or Firm* — Sughrue Mion, PLLC

(57) ABSTRACT

The present invention relates to a novel long-acting palmitic acid-conjugated gonadotrophin-releasing hormone (GnRH) derivative and a pharmaceutical composition containing the same. A GnRH derivative of the present invention is expected to greatly contribute, through excellent bioavailability and increased half-life in blood, to the reduction in drug dosing frequency and dosage and the like in the treatment of sex hormone-dependent diseases. Particularly, the GnRH derivative can overcome the disadvantages of existing GnRH sustained-release preparations, which have the side effects of residual feeling and pain at the injection site.

5 Claims, 6 Drawing Sheets
Specification includes a Sequence Listing.

SEQUENCE LISTING

<160> NUMBER OF SEQ ID NOS: 6

<210> SEQ ID NO 1
<211> LENGTH: 10
<212> TYPE: PRT
<213> ORGANISM: homo sapiens
<220> FEATURE:
<221> NAME/KEY: SITE
<222> LOCATION: (1)..(1)
<223> OTHER INFORMATION: Glu in position 1 is pyroGlu.

<400> SEQUENCE: 1

Glu His Trp Ser Tyr Gly Leu Arg Pro Gly
1               5                   10

<210> SEQ ID NO 2
<211> LENGTH: 9
<212> TYPE: PRT
<213> ORGANISM: Artificial Sequence
<220> FEATURE:
<223> OTHER INFORMATION: GnRH analog-Leuprolide
<220> FEATURE:
<221> NAME/KEY: SITE
<222> LOCATION: (1)..(1)
<223> OTHER INFORMATION: Glu in position 1 is pyroGlu.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminal of the peptide was modified as
      NHEt(des-Gly).

<400> SEQUENCE: 2

Glu His Trp Ser Tyr Leu Leu Arg Pro
1               5

<210> SEQ ID NO 3
<211> LENGTH: 9
<212> TYPE: PRT
<213> ORGANISM: Artificial Sequence
<220> FEATURE:
<223> OTHER INFORMATION: GnRH analog
<220> FEATURE:
<221> NAME/KEY: SITE
<222> LOCATION: (1)..(1)
<223> OTHER INFORMATION: Glu in position 1 was modified with Palmitate.
<220> FEATURE:
<221> NAME/KEY: PEPTIDE
<222> LOCATION: (1)..(9)
<223> OTHER INFORMATION: The petide was sallificated with sadium salt.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminus of the peptide was modified as
      NHEt(des-Gly).

<400> SEQUENCE: 3

Glu His Trp Ser Tyr Leu Leu Arg Pro
1               5

<210> SEQ ID NO 4
<211> LENGTH: 9
<212> TYPE: PRT
<213> ORGANISM: Artificial Sequence
<220> FEATURE:

```
<223> OTHER INFORMATION: GnRH analog
<220> FEATURE:
<221> NAME/KEY: SITE
<222> LOCATION: (1)..(1)
<223> OTHER INFORMATION: Gln in position 1 was modified with Palmitate.
<220> FEATURE:
<221> NAME/KEY: PEPTIDE
<222> LOCATION: (1)..(9)
<223> OTHER INFORMATION: The petide was sallificated with sadium salt.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminus of the peptide was modified as
      NHEt(des-Gly).

<400> SEQUENCE: 4

Gln His Trp Ser Tyr Leu Leu Arg Pro
1               5

<210> SEQ ID NO 5
<211> LENGTH: 9
<212> TYPE: PRT
<213> ORGANISM: Artificial Sequence
<220> FEATURE:
<223> OTHER INFORMATION: GnRH analog
<220> FEATURE:
<221> NAME/KEY: SITE
<222> LOCATION: (1)..(1)
<223> OTHER INFORMATION: Glu in position 1 was modified with Palmitate.
<220> FEATURE:
<221> NAME/KEY: PEPTIDE
<222> LOCATION: (1)..(9)
<223> OTHER INFORMATION: The petide was sallificated with acetate salt.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminus of the peptide was modified as
      NHEt(des-Gly).

<400> SEQUENCE: 5

Glu His Trp Ser Tyr Leu Leu Arg Pro
1               5

<210> SEQ ID NO 6
<211> LENGTH: 9
<212> TYPE: PRT
<213> ORGANISM: Artificial Sequence
<220> FEATURE:
<223> OTHER INFORMATION: GnRH analog
<220> FEATURE:
<221> NAME/KEY: SITE
<222> LOCATION: (1)..(1)
<223> OTHER INFORMATION: Gln in position 1 was modified with Palmitate.
<220> FEATURE:
<221> NAME/KEY: PEPTIDE
<222> LOCATION: (1)..(9)
<223> OTHER INFORMATION: The petide was sallificated with acetate salt.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminus of the peptide was modified as
      NHEt(des-Gly).
```

-continued

```
<400> SEQUENCE: 6

Gln His Trp Ser Tyr Leu Leu Arg Pro
1               5
```

LONG-ACTING PALMITIC ACID-CONJUGATED GNRH DERIVATIVE, AND PHARMACEUTICAL COMPOSITION CONTAINING SAME

CROSS REFERENCE TO RELATED APPLICATIONS

This application is a National Stage of International Application No. PCT/KR2018/006954, filed on Jun. 20, 2018, which claims priority from Korean Patent Application No. 10-2017-0125291, filed on Sep. 27, 2017, the entire disclosures of which are incorporated herein by reference.

TECHNICAL FIELD

The present disclosure relates to a novel long-acting palmitic acid-conjugated derivative of gonadotrophin-releasing hormone (GnRH) and a pharmaceutical composition containing the same.

BACKGROUND

In general, a gonadotrophin-releasing hormone (GnRH) or a luteinizing hormone-releasing hormone is a hypothalamic neurohormone and is a type of neuroendocrine peptide. Specifically, GnRH is synthesized in the neurovascular terminal cells of the hypothalamus and acts on gonadotropic cells in the anterior pituitary gland to promote the synthesis and release of luteinizing hormone (LH) or follicle stimulating hormone (FSH), which are both gonadotrophins. Luteinizing hormones or follicle stimulating hormones, the synthesis and release of which are controlled by GnRH, play a role in controlling male and female sex hormones and maturing reproductive cells.

It is known that, while GnRH has the effect of promoting the secretion of gonadotropin or ovulation at normal concentrations, it has an antagonistic inhibitory effect at high concentrations, which is contradictory. A high dose of GnRH may be used to treat prostate cancer or breast cancer, which are hormone-dependent tumors, as well as endometriosis, uterine fibroids, central precocious puberty, and adenomyosis, etc. It is also widely known that GnRH or GnRH derivatives can be used in the treatment of various sex hormone-dependent diseases (Kumar P. and Sharma A, J Hum Reprod Sci, 2014; 7(3): pp. 170-174).

As for commercially available therapeutic agents comprising GnRH, there exist sustained release products designed to be injected every one or three months, which are in the form of a biodegradable multinuclear storage microcapsules (PLGA or PLA) containing a GnRH agonist. Particularly, a sustained-release product comprising a GnRH derivative under the brand name of Lupron® Depot is commercially available. This commercial product contains PLGA [poly(lactic-co-glycolic acid)] microspheres as a sustained release ingredient, with the GnRH derivative of leuprolide acetate as an active ingredient. Due to the use of a biodegradable polymer, Lupron Depot® must be intramuscularly or subcutaneously administered at a large dose. In this regard, pain or tissue injury is accompanied at the injection site and a lump remains at the site for several months, with the occasional incidence of inflammation, since the biodegradable polymers are not completely absorbed even after one month.

In order to overcome these drawbacks of Lupron Depot®, although other products including Eligard® have been additionally developed, they are still disadvantageous in terms of the initial drug release, low drug stability in a mixed solution phase, etc. There is thus a continuing need for developing formulations or dosage forms which allow high blood levels of GnRH to be maintained for a prolonged period of time.

Existing GnRH sustained-release products, which are intended to slowly release GnRH into blood, contain additional sustained release ingredients for releasing the active ingredient over a prolonged period of time. Accordingly, the total dose of the products increases, which lead to problems of pain, residual feeling at the injection site, low drug stability, etc. Particularly, among the patients who had received the existing products (leuprolide acetate), as much as 23 to 30% of the patients complained about pain at the injection sites (Lee P A et al., J. Clin, Endocrinol Metab, 2014).

Meanwhile, U.S. Pat. No. 9,694,051 discloses that a conjugated adrenomedullin peptide where an alkyl moiety is conjugated to lysine (Lys) at the N-terminals of some adrenomedullin peptides has an increased half-life in blood. Although an increase in the half-life in blood of the peptide is exhibited by conjugating an alkyl moiety to the N-terminal of the peptide, the peptide is quite different from GnRH in terms of function and sequence. Also, the peptide differs from GnRH in that the terminal amino residue of the peptide to which the alkyl moiety is conjugated is lysine.

Under such circumstances, the present inventor has made efforts to develop a long-acting GnRH formulation in which the GnRH itself has a prolonged in vivo half-life and increased bioavailability, unlike the existing sustained-release formulations which have disadvantages due to the additional ingredients or formulation design for sustained release, etc. Specifically, a long-acting palmitic acid-conjugated GnRH derivative was prepared by conjugating palmitic acid to a GnRH derivative which is designed to have an increased in vivo half-life of GnRH and converting the conjugate to a specific salt form. The long-acting palmitic acid-conjugated GnRH derivative was found to exhibit excellent bioavailability and a prolonged in vivo half-life and maintain a high blood level, which led to the present invention.

The long-acting palmitic acid-conjugated GnRH derivative according to the present disclosure and a pharmaceutical composition containing the same can be used for the prevention and treatment of various sex hormone-dependent diseases or for contraception.

SUMMARY

In consideration of the above problems with the existing sustained release formulations, the present invention aims to develop a long-acting GnRH formulation having increased bioavailability and in vivo half-life of GnRH, which is as short as 2 to 4 min in circulating blood. Thus, the purpose of the present invention is to provide a long-acting palmitic acid-conjugated GnRH derivative with ease of administration and improved efficacy and a pharmaceutical composition containing the same.

Through thorough and intensive research to prepare a GnRH derivative having an increased bioavailability and in vivo half-life of GnRH itself, which has a circulating half-life of as short as 2 to 4 min in the natural form, the present inventor developed a long-acting palmitic acid-conjugated GnRH derivative comprising palmitic acid conjugated to GnRH and a pharmaceutically acceptable salt and found that it has an improved efficacy and in vivo half-life, and thus arrived at the present disclosure.

As used herein, the term "improved efficacy" of a long-acting palmitic acid-conjugated GnRH derivative means that it has a higher therapeutic effect on sex hormone-related diseases at the same concentration with a natural GnRH. For example, it means that the long-acting palmitic acid-conjugated GnRH derivative has higher cytotoxic effects on prostate cancer or breast cancer when administered at the same dose as a natural GnRH.

GnRH has the effect of promoting the release of gonadotropins or ovulation at normal concentration, while it has antagonistic inhibitory effects at high concentrations which is contradictory. Accordingly, high concentrations of GnRH inhibit the progression of diseases aggravated by sex hormones or are effective for the alleviation and treatment of sex hormone-dependent diseases.

Hereinafter, a detailed description will be provided with respect to the long-acting palmitic acid-conjugated GnRH derivative, which comprises a GnRH derivative; palmitic acid conjugated to the GnRH derivative; and a pharmaceutically acceptable salt, and a pharmaceutical composition containing the same according to the present disclosure.

※ Long-Acting, Palmitic Acid-Conjugated GnRH Derivative

Gonadotropin-releasing hormone (GnRH) is a hormone synthesized in the neurovascular terminal cells of the hypothalamus and acts on gonadotropic cells in the anterior pituitary gland to promote the synthesis and release of luteinizing hormone (LH) or follicle stimulating hormone (FSH), which are both gonadotrophins. GnRH may differ in sequence from one species to another. Mammalian natural GnRH may have the amino acid sequence of SEQ ID NO: 1 as follows.

```
[Mammalian GnRH sequence]
                                  (SEQ ID NO: 1)
pGlu-His-Trp-Ser-Tyr-Gly-Leu-Arg-Pro-Gly
```

The GnRH derivative of the present disclosure is structurally analogous to GnRH, but may act in a different manner in vivo. At an early stage after being administered, the GnRH derivative, particularly corresponding to a GnRH agonist, binds to a GnRH receptor to promote the in vivo synthesis and secretion of follicle stimulation hormone (FSH) and luteinizing hormone (LH) to a certain level. However, the continuous maintenance of the GnRH derivative concentration in vivo depletes gonadotropins and down-regulates the GnRH receptor, resulting in a contradictory effect that the synthesis and secretion of FSH and LH are rather suppressed. Through such effects, the GnRH derivatives can thus be used for preventing or treating sex hormone-dependent diseases and as a contraceptive.

In one embodiment of the present disclosure, the GnRH derivative is a GnRH agonist, which may be selected from the group consisting of leuprolide, goserelin, triptorelin, nafarelin, buserelin, histrelin, deslorelin, meterelin, gonadorelin, and modified derivatives thereof.

In another embodiment of the present disclosure, the GnRH derivative has a sequence that has at least 80%, at least 85%, at least 90%, at least 95%, or at least 98% homology to the existing GnRH agonists.

Particularly, the GnRH derivative of the present disclosure may have a sequence that has at least 80%, at least 85%, at least 90%, at least 95%, or at least 98% homology to GnRH, leuprolide, goserelin, triptorelin, nafarelin, buserelin, histrelin, deslorelin, meterelin, or gonadrelin and, more particularly, a sequence that has at least 80%, at least 85%, at least 90%, at least 95%, or at least 98% homology to GnRH (SEQ ID NO: 1) or leuprolide (SEQ ID NO: 2).

In an embodiment of the present disclosure, a GnRH derivative is a modified leuprolide where glutamic acid of the first amino acid on leuprolide is substituted with a different amino acid, more particularly with glutamine.

In an embodiment of the present disclosure, the GnRH derivative may have the amino acid sequence of SEQ ID NO: 2, 3, or 4.

Particularly, a GnRH derivative of the present disclosure may mean a derivative having an additional modification of the existing GnRH or GnRH derivative.

Specifically, the GnRH derivative of the present disclosure may be a long-acting palmitic acid-conjugated GnRH derivative comprising: palmitic acid conjugated to a GnRH derivative; and a pharmaceutically acceptable salt. More particularly, the palmitic acid may be conjugated to the amino terminus of the GnRH derivative.

As used herein, the term "palmitic acid" is a carboxyl of a hydrocarbon chain which is a hydrophobic normal saturated fatty acid of 16 carbon atoms and has one carboxyl group (—COOH).

Through the conjugation with palmitic acid, the long-acting GnRH derivative of the present disclosure has the following advantages: i) enhanced renal reabsorption and fat storage efficiency; ii) protection effect resulting from increased binding with serum proteins; iii) delayed renal clearance resulting from increased hydrophobicity of analog series; and iv) increase in release time and pharmaceutical efficacy resulting from attaching to lipid membranes or biological membranes.

An emulsion of dexamethasone palmitate where palmitic acid is conjugated to dexamethasone is known to exhibit an anti-inflammatory effect 5.6-fold higher than dexamethasone alone at the same dose (Peng et al., Drug Development and Industrial Pharmacy, 2010: 36(12)). Commercially available, long-acting products which are formulated by fatty acid conjugation are exemplified by INVEGA TRINZA® where paliperidone is conjugated with a fatty acid and Lipotalon® where dexamethasone is conjugated with a fatty acid.

It is known that when a palmitic acid is conjugated to hormones or enzymes, the in vivo half-life of the hormones or enzymes is increased due to the above mechanism. However, their water solubility may be significantly decreased due to the increased hydrophobicity of the molecule. Further, intermolecular aggregation in a water-soluble environment or intramolecular hydrophobic bonds at hydrophobic sites of the protein may be caused. Hence, the conjugated proteins may suffer from the disadvantage of decreases in stability of the formulation, bioavailability, and protein activity.

In this regard, there is a need for an appropriate formulation strategy for increasing the in vivo half-life of proteins through conjugation with palmitic acid, without decreasing the efficacy of the specific protein or causing protein aggregation.

As used herein, a "pharmaceutically acceptable salt" is intended to encompass all pharmaceutically acceptable salts that can be used for the purpose of increasing the stability, water solubility, bioavailability, etc., of the palmitic acid-conjugated GnRH derivative of the present disclosure, without limitations thereto.

In one embodiment of the present disclosure, the pharmaceutically acceptable salt is selected from the group consisting of inorganic acids, organic acids, ammonium salts, alkali metal salts, and alkaline earth metal salts. In another embodiment, the pharmaceutically acceptable salt is selected from the group consisting of hydrochloride, hydrobromide, phosphate, metaphosphate, nitrate, sulfate, acetate, sulfonate, benzoate, citrate, ethanesulfonate, fumarate, lactate, maleate, malate, succinate, tartrate, sodium salt, calcium salt, potassium salt, and magnesium salt.

In one embodiment of the present disclosure, the palmitic acid-conjugated GnRH derivative of the present disclosure comprises the amino acid sequence of SEQ ID NO: 3 or 4, wherein palmitic acid is conjugated to the amino terminus of the GnRH derivative, and the pharmaceutically acceptable salt is sodium salt or acetate.

In another embodiment of the present disclosure, the palmitic acid-conjugated GnRH derivative of the present disclosure comprises the amino acid sequence of SEQ ID NO: 3, wherein palmitic acid is conjugated to the amino terminus of the GnRH derivative, and the pharmaceutically acceptable salt is acetate.

In a further embodiment of the present disclosure, the palmitic acid-conjugated GnRH derivative of the present disclosure comprises the amino acid sequence of SEQ ID NO: 4, wherein palmitic acid is conjugated to the amino terminus of the GnRH derivative, and the pharmaceutically acceptable salt is sodium salt.

X. Pharmaceutical Composition Comprising Palmitic Acid-Conjugated GnRH Derivative The pharmaceutical composition of the present disclosure comprises the palmitic acid-conjugated GnRH derivative of the present disclosure, with no limitations imparted thereto.

In an embodiment of the present disclosure, the pharmaceutical composition of the present disclosure comprises a pharmaceutically effective amount of the palmitic acid-conjugated GnRH derivative of the present disclosure and may further comprise a pharmaceutically acceptable carrier. As used herein, the term "pharmaceutically effective amount" means a sufficient amount to achieve the efficacy or activity of the palmitic acid-conjugated GnRH derivative of the present disclosure.

Pharmaceutically acceptable carriers which can be included in the pharmaceutical composition of the present disclosure are those commonly used for preparing a formulation, and examples of the pharmaceutically acceptable carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but are not limited thereto.

In addition to the above ingredients, the pharmaceutical composition of the present disclosure may further comprise a lubricant, a humectant, a sweetener, a flavorant, an emulsifier, a suspending agent, a preservative, and the like.

The pharmaceutical composition of the present disclosure may be administered orally or parenterally. Particularly, for injection routes, it may be administered in a dosage form of either a subcutaneous injection or an intramuscular injection. A dosage form may be selected in consideration of various factors, such as the effect of controlling in vivo concentrations.

Accordingly, the pharmaceutical composition of the present disclosure may be preferably a dosage form selected from an injection, a paste, a gelling agent, a lotion, a capsule, a tablet, a liquid, a suspension, a sprayer, an inhaler, an eye drop, an adhesive, and a patch, particularly preferably an injection.

The suitable dosage of the pharmaceutical composition of the present disclosure varies depending on factors including the formulation method, dosing method, patient's age, body weight, gender and morbidity, food, administration time, administration route, excretion rate, and response sensitivity. The pharmaceutical composition of the present disclosure is generally administered at a dose of 0.001-100 mg/kg for an adult. The pharmaceutical composition comprises the palmitic acid-conjugated GnRH derivative of the present disclosure in an amount of about 0.001-30 mg/mL.

The pharmaceutical composition of the present disclosure is formulated using a pharmaceutically acceptable carrier and/or excipient, according to a method that can be easily carried out by a person having ordinary skill in the art. The pharmaceutical composition of the present disclosure may be prepared into a unit dosage form or may be inserted into a multi-dose container. In this regard, the formulation may be in the form of a solution, a suspension, a syrup, or an emulsion in an oil or aqueous medium or in the form of an extract, powder, granules, a tablet, or a capsule and may further comprise a dispersant or a stabilizer.

The pharmaceutical composition of the present disclosure may be used for the prevention or treatment of a sex hormone-dependent disease or for contraception. The sex hormone-dependent disease may be selected from the group consisting of prostate cancer, breast cancer, ovarian cancer, endometriosis, uterine fibroid, polycystic ovary disease, central precocious puberty, hypertrichosis, gonadotroph pituitary adenoma, sleep apnea, irritable bowel syndrome, premenstrual syndrome, benign prostatic hyperplasia, and contraception, but is not limited thereto.

When used in combination with a conventional biodegradable polymer, the pharmaceutical composition of the present disclosure may exhibit a remarkably excellent in vivo half-life. Accordingly, the pharmaceutical composition of the present disclosure may further comprise biodegradable polymers. In the present invention, the biodegradable polymer allows a drug to be delivered to parenteral routes through the body, or allows the polymer comprising the GnRH derivative of the present disclosure to topically act on a specific site. With respect to the biodegradable polymer in the present disclosure, Chasin M et al. ("Biodegradable Polymers as Drug Delivery Systems", New York, Marcel Dekker, 1990) or D. Wescman et al. ("Handbook of Biodegradable Polymers", Taylor & Francis, 1998) may be referred to, without being limited thereto.

For example, the biodegradable polymer of the present disclosure may be PLA (poly-lactic acid), linear or branched PLGA (poly(lactic-co-glycolic acid)), PGA (poly-glycolic acid), hydrogel, or the like.

The present disclosure further provides methods and use for preventing or treating a sex hormone-related symptom or disease by administering the palmitic acid-conjugated GnRH derivative of the present disclosure or a composition containing the same.

The excellent bioavailability and extended in vivo half-life in the novel gonadotrophin-releasing hormone (GnRH) derivative of the present disclosure is expected to make great contributions to the reduction in dosing frequency and dosage. Particularly, the long-acting palmitic acid-conjugated GnRH derivative could overcome the problems with the existing sustained release GnRH formulations, such as the adverse effects of residual feeling and pain at the injection site.

DETAILED DESCRIPTION

Figure 1:
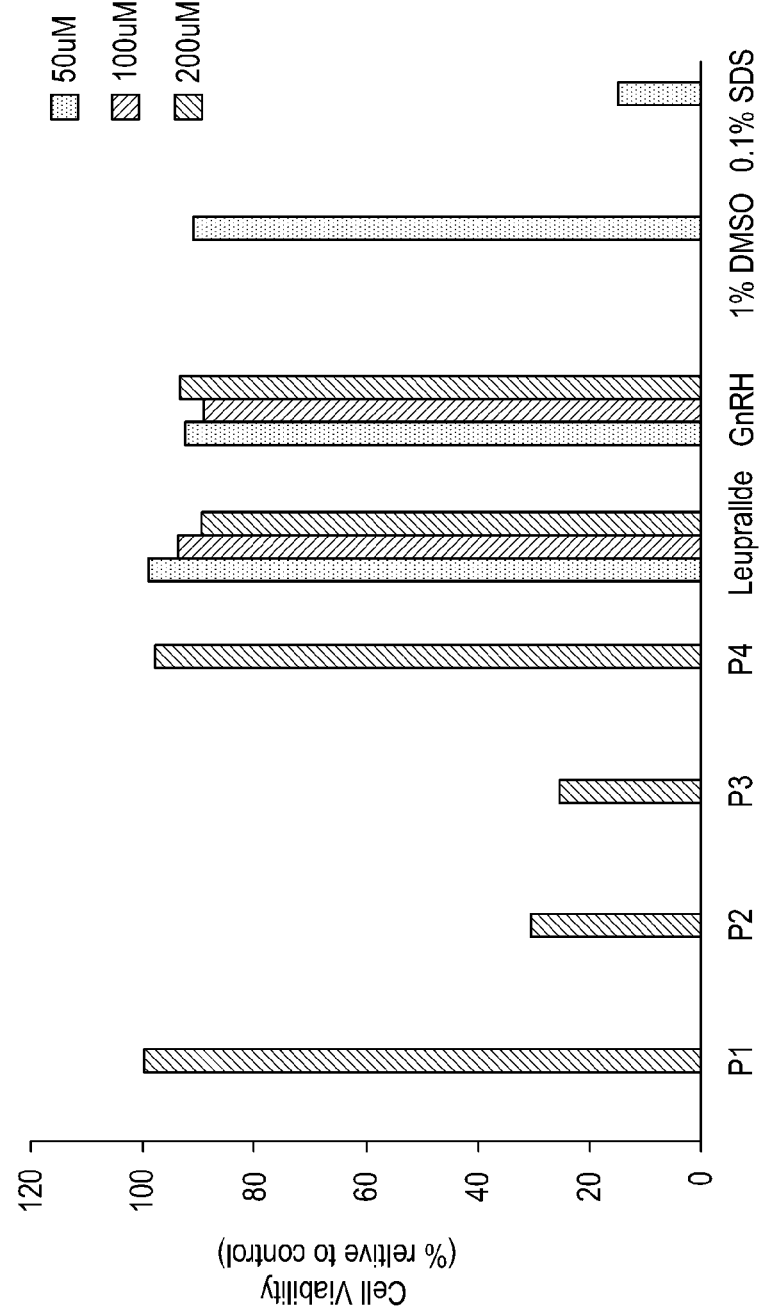
FIG. 1 is a graph showing the cell viability of the prostate cancer cell line DU-145 after treatment with various concentrations of GnRH or GnRH derivatives and the control drug. 1% DMSO was used as a negative control and 0.1% SDS as a positive control.

Hereinafter, the embodiments of the present disclosure will be described by referring to Preparation Examples and Examples, which are set forth to illustrate the present disclosure, but not construed to limit the present invention.

Preparation Example 1: Preparation Method for Gonadotrophin-Releasing Hormone (GnRH) Derivative Natural mammalian GnRH has the following sequence.

[Mammalian GnRH sequence]
(SEQ ID NO: 1)
pGlu-His-Trp-Ser-Tyr-Gly-Leu-Arg-Pro-Gly Leuprolide® having the mammalian GnRH sequence with the substituted D-Leu instead of Gly at position 6 and the substituted des-Gly instead of Gly at position 10 was used as a backbone for the GnRH derivative and the palmitic acid-conjugate GnRH derivative of the present disclosure.

[Leuprolide Sequence]
(SEQ ID NO: 2)
pGlu-His-Trp-Ser-Tyr[D-Leu6]-Leu-Arg-Pro-NHEt Derivatives where glutamate at position 1 on the Leuprolide sequence remains unsubstituted or was substituted with glutamine were prepared as follows.

(1) Preparation Method for GnRH Derivative Peptides

The derivatives are synthesized using a general Fmoc/tBu solid-phase peptide synthesis (SPPS) method, where the α-amino groups of amino acid residues are protected by the base-labile group of Fmoc (fluorenylmethyloxycarbonyl chloride) while the side groups are protected by an acid-labile group. In the solid phase peptide synthesis method comprising the following steps, a peptide chain is sequentially extended by repetitive Fmoc cleavage and amino acid coupling.

① Load Fmoc amino acid onto resin (Fmoc-Pro-trityl resin);
② Remove Fmoc protecting group from Fmoc-AA-resin (20% piperidine/DMF);
③ Wash with DMF;
④ Bind amino acid after activation (DIC/HOBt used);
⑤ Wash with DMF;
⑥ Repeat steps ② to ⑤ to bind amino acids sequentially;
⑦ Remove resin only from synthesized peptide (1.5 TFA/DCM);
⑧ Attach ethylamine to the amino terminus of the resulting peptide (using EDC.HCl/HOAt); and
⑨ Make overall cleavage of protected side chains from the resulting peptide (92.5% TFA/2.5% TIS/2.5% EDT/2.5% H2O).

Palmitic acid was conjugated to the amino terminus of the obtained GnRH derivative. Conjugating palmitic acid to the amino terminus of the derivative was carried out in the same manner as the conjugation of general amino acids.

(2) Purification of GnRH Derivative Peptides

Following the TFA cleavage, the peptide was purified using a C18 column in the Shimadzu HPLC 10AVP system under HPLC conditions (A buffer 0.05% TFA/$H_2O$, B buffer 0.05% TFA/acetonitrile, flow rate 1 mL/min, wavelength 230 nm). In Table 1, P1 and P3 GnRH derivatives have glutamate as the amino acid residue at position 1, while P2 and P4 GnRH derivatives have glutamine as the amino acid residue at position 1.

TABLE 1

| GnRH derivative | Purity (%) | MS Calculated (Da) | MS Measured (Da) |
|---|---|---|---|
| P1 | 98.2 | 1465.8 | 1465.7 |
| P2 | 98.2 | 1464.8 | 1464.9 |
| P3 | 98.1 | 1465.8 | 1465.5 |
| P4 | 98.3 | 1464.8 | 1464.0 |

Palmitic acid is sparingly soluble in water with a solubility of 0.04 mg/ml and exists as a solid phase at room temperature with a melting point of 60° C. Hence, as the palmitic acid-conjugated GnRH derivative might be poorly soluble in water, salting was further carried out. The palmitic acid-conjugated GnRH derivatives were subjected to salting with sodium salt or acetate to prepare P1 to P4 palmitic acid-conjugated GnRH derivative salts as shown in Table 2 below.

TABLE 2

| Derivative | Backbone/Derivative sequence and salt |
|---|---|
| GnRH | pyroGlu-His-Trp-Ser-Tyr-Gly-Leu-Arg-Pro-Gly-NH₂ (SEQ ID NO: 1) |
| Leuprolide | pyroGlu-His-Trp-Ser-Tyr-$_D$Leu-Leu-Arg-Pro-NHEt (SEQ ID NO: 2) |
| P1 | Palmitate-Glu-His-Trp-Ser-Tyr-$_D$Leu-Leu-Arg-Pro-NHEt sodium salt (SEQ ID NO: 3) |
| P2 | Palmitate-Gln-His-Trp-Ser-Tyr-$_D$Leu-Leu-Arg-Pro-NHEt sodium salt (SEQ ID NO: 4) |
| P3 | Palmitate-Glu-His-Trp-Ser-Tyr-$_D$Leu-Leu-Arg-Pro-NHEt acetate salt (SEQ ID NO: 5) |

TABLE 2-continued

| Derivative | Backbone/Derivative sequence and salt |
|---|---|
| P4 | Palmitate-Gln-His-Trp-Ser-Tyr-$_D$Leu-Leu-Arg-Pro-NHEt acetate salt (SEQ ID NO: 6) |

Subsequent experiments were performed using the prepared GnRH derivatives and palmitic acid-conjugated GnRH derivative salts.

Example 1: Effect of Palmitic Acid Conjugation on Prostate Cancer Cell Death GnRH derivatives are clinically applied to the treatment of diseases including breast cancer, prostate cancer, endometriosis, central precocious puberty, and the like. The DU-145 cell line, which is a type of prostate cancer cells, was cultured in T75 flasks containing an adequate amount of RPIM 1640 culture medium (containing 10% FBS, penicillin/streptomycin, and 1% non-essential amino acids) in a sterile incubator having 5% $CO_2$/95% air at 37° C. Cell death assay was performed using the Cell Counting Kit-8 (CCK-8, manufactured by DOJINDO). The DU-154 cells were separated from the T75 flasks by trypsinization treatment and transferred to 96-well plates at a density of 1×104 cells/well, followed by incubation for one hour for attachment.

Figure 2:
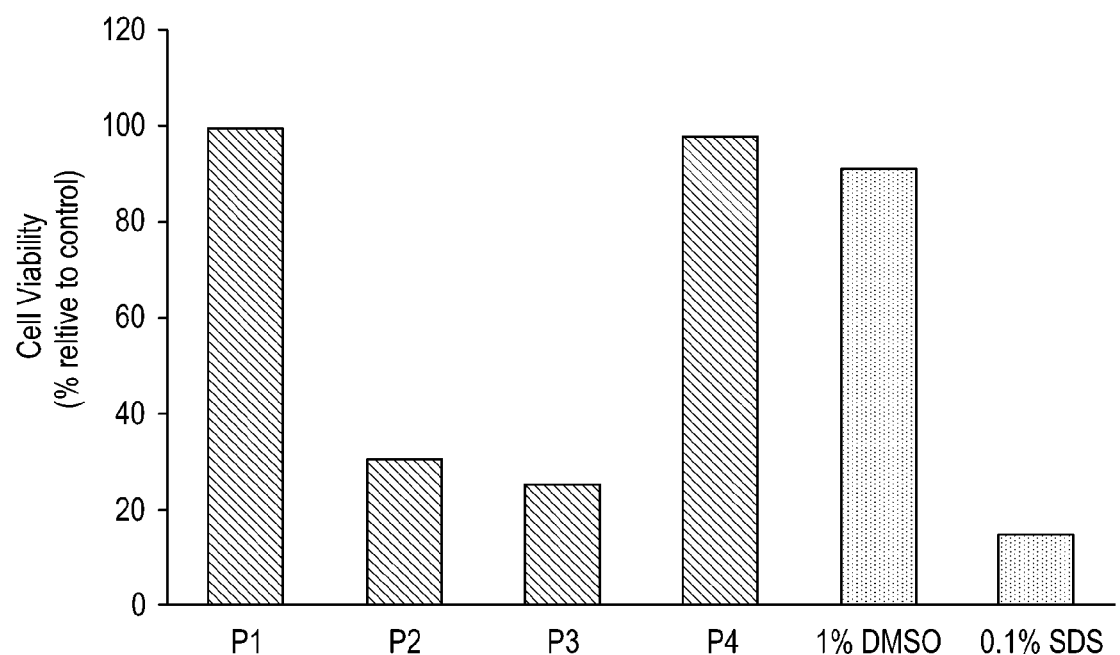
FIG. 2 is a graph showing the cell viability of the prostate cancer cell line DU-145 after treatment with sodium or acetate salt of GnRH derivatives and the control drug. 1% DMSO was used as a negative control and 0.1% SDS as a positive control.

Subsequently, the cells were treated with various concentrations of GnRH or GnRH derivatives, and control reagents. Specifically, 1% DMSO was used as a negative control for cell death while 0.1% SDS served as a positive control. After 48 hours of incubation, the existing culture medium was removed, and 100 μL of fresh culture medium and 10 μL of CCK-8 solution were applied to each well. Again, after 48 hours of incubation, the medium solution was replaced by 100 μL of fresh culture medium and 10 μL of CCK-8 solution. The cells were incubated for 4 hours, and then the absorbance was measured at 450 nm to assess cell viability. The measurement results are provided in Table 3 and FIGS. 1 and 2.

TABLE 3

| Derivative | Treatment conc. (μM) | Viability relative to control (%) | Statistical significance (compared to 1% DMSO control) |
|---|---|---|---|
| P1 | 200 | 99.7 | |
| P2 | 200 | 30.7 | <0.0001 |
| P3 | 200 | 25.8 | <0.0001 |
| P4 | 200 | 98.3 | |
| Leuprolide | 50 | 99.1 | |
| | 100 | 93.6 | |
| | 200 | 89.7 | |
| GnRH | 50 | 90.9 | |
| | 100 | 88.7 | |
| | 200 | 93.4 | |
| 1% DMSO | | 91.0 | |
| 0.1% SDS | | 21.7 | <0.0001 |

The P2 and P3 derivatives were observed to exhibit about 7- to 7.5-fold greater cytotoxic effects, compared to Leuprolide or GnRH, which exhibits a cell death rate of about 10% on prostate cancer cells. The results suggest that combinations of amino acid substitution at position 1 and salting bring about unpredicted excellent cytotoxic effects on prostate cancer cells.

GnRH derivatives significantly differ from each other in terms of the cytotoxic effect on prostate cancer cell lines, depending on the type of the first amino acids and salting.

Example 2: Differences in Solubility of Palmitic Acid-Conjugated GnRH Derivative by Saltine Type The solubility of GnRH in water is estimated to be about 1 mg/mL under experimental conditions and about 0.0588 mg/mL under real conditions. In contrast, acetate is known to increase the solubility of GnRH about 10 times or more to 10 mg/mL (https://www.drugbank.ca/drugs/DB00644).

The salt is understood to increase the solubility by lowering the pH of the solvent, along with ionization thereof. In order to increase the solubility of commercially available GnRH and GnRH derivatives, various linkages were tried at the carboxy terminal (C terminal) of GnRH and GnRH derivatives, as summarized in Table 4 below.

TABLE 4

| Product Name | Treatment concentration | Dose (Strength) | Salt type at C terminal |
|---|---|---|---|
| Factrel Inj. 0.5 mg/vial | Powder, for solution | 0.5 mg | GnRH hydrochloride |
| Factrel Pws 100 mcg/vial | Powder, for solution | 100 mcg | |
| Factrel Pws 500 mcg/vial | Powder, for solution | 500 mcg | |
| Lutrepulse | Powder, for solution | 3.2 mg | GnRH acetate |
| Lutrepulse Pws 0.8 mg/vial | Powder, for solution | 0.8 mg | |

The water solubilities of commercially available GnRH derivative salts are provided as shown in Table 5 below.

TABLE 5

| Ingredient | CAS No. | Avg. Weight (Da) | Water solubility |
|---|---|---|---|
| GnRH | 33515-09-2 | 1182.2901 | 1 mg/mL |
| GnRH acetate | 52699-48-6 | 1260.378 | 10 mg/mL |
| GnRH hydrochloride | 51952-41-1 | 1218.77 | 0.0498 mg/mL |

Additionally, the four types of palmitic acid-conjugated GnRH derivatives were subjected to a solubility test. First, the peptides in the form of powder at room temperature were weighed with a microbalance and dissolved in the organic solvent 100% DMSO with a final concentration of 20 mM. They were all observed with the naked eye to dissolve very quickly and completely. The obtained solutions were used as stocks and diluted in various concentrations in PBS buffer solutions or cell culture medium to examine the solubility thereof.

Figure 3:
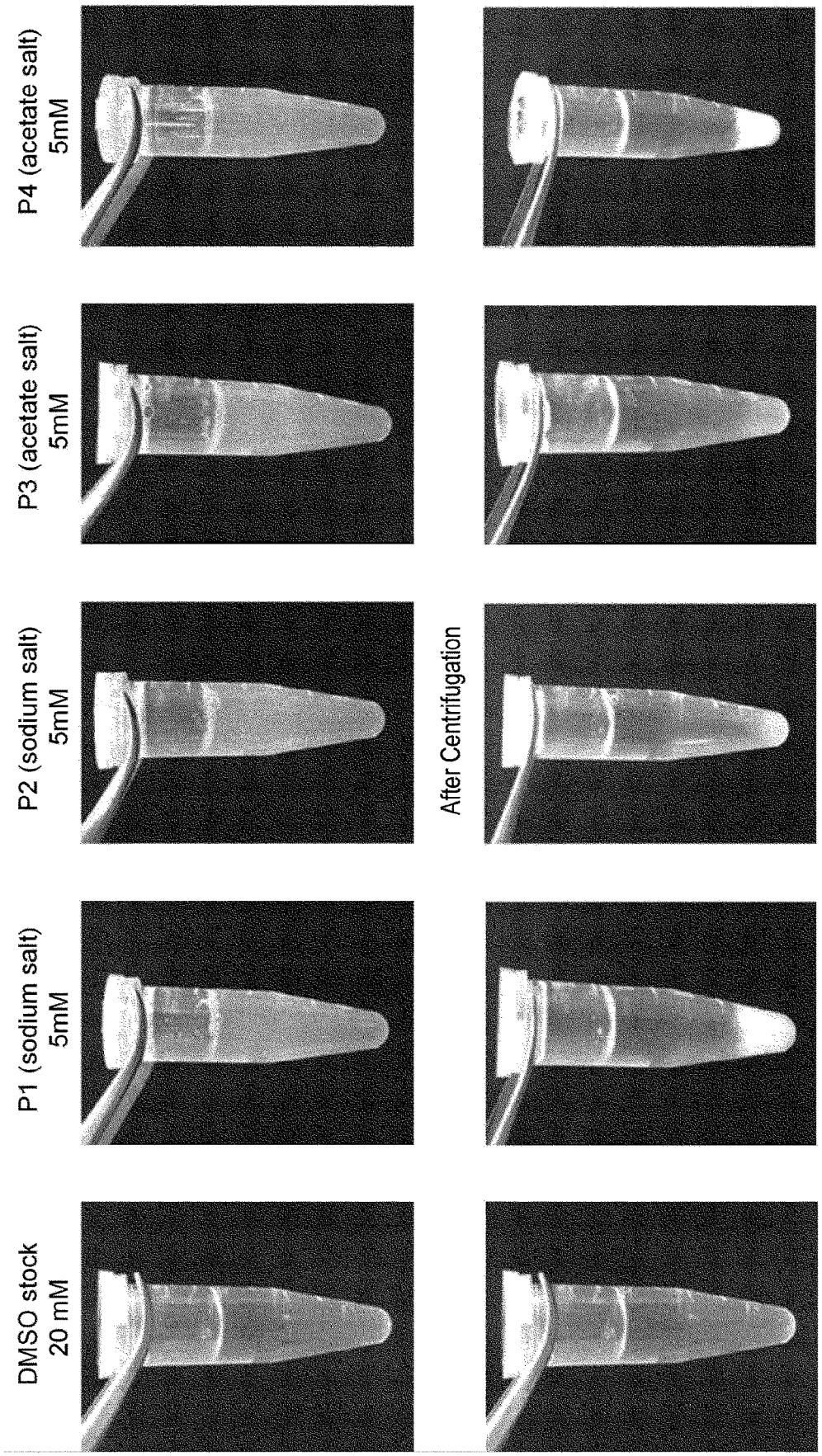
FIG. 3 shows the results of measuring the solubility of the palmitic acid-conjugated GnRH derivatives having different first amino acid residues and salt types.

When the peptide stocks were diluted in PBS buffer solutions or cell culture medium, the solutions became milky, with the generation of aggregates. The degree of the aggregation differed in each GnRH derivative types. The degree of aggregation was examined by centrifuging the aggregates. As a result, P2 and P3 derivatives, which were identified to have excellent cytotoxic effects on prostate cancer cell lines, were observed to be very high in solubility (FIG. 3).

In the two derivatives, sodium salt and acetate, respectively, were conjugated to the carboxyl terminal of GnRH, which indicates that the solubility of the palmitic acid-conjugated GnRH derivatives of the present disclosure is influenced by the type of the first amino acid residues and salting.

Example 3: Measurement of Increase Rate of In Vivo Half-Life

The present inventor carried out animal experiments (female SD rats, nine weeks old) in order to examine the increased in vivo half-lives of the prepared palmitic acid-conjugated GnRH derivatives. In brief, Leuprolide (n=6), Leuprolide acetate depot formulation for one-month administration (3.75 mg/month; n=7), and GnRH derivative P2 (n=6) or P4 (n=6) were subcutaneously administered once at a dose of 12.5 mg/kg to rats of each group, followed by a monitoring of blood concentrations over time. Before administration and at 0.5, 1, 2, and 6 hours and on days 1, 3, 7, 10, 14, 21, and 28 after administration, blood samples were taken from the tail vein of the rats and measured for the blood concentrations of Leuprolide and GnRH derivatives, using LC/MSMS. If the concentration reached about 4 ng/mL at a specific time point, no measurements were further made for the next time point.

The experimental results are summarized as follows.

TABLE 6

| Time | Comparative Example 1 (natural) Leuprolide | | Comparative Example 2 (sustained release) Leuprolide acetate (3.75 mg) | | P2 Pal_[Q1]GnRH | | P4 Pal_[Q1]GnRH AcOH | |
|---|---|---|---|---|---|---|---|---|
| | Mean | S.D. | Mean | S.D. | Mean | S.D. | Mean | S.D. |
| 0 | — | — | — | — | — | — | — | — |
| 0.5 hr. | 1020 | 177 | 133 | 54.1 | 11.8 | 4362 | 6.51 | 2.30 |
| 1 hr. | 769 | 572 | 164 | 89.1 | 16.9 | 3.16 | 9.22 | 2.57 |
| 2 hr. | 228 | 267 | 93.0 | 51.5 | 29.1 | 4.97 | 18.6 | 2.83 |
| 6 hr. | 2.88 | 4.09 | 19.6 | 7.04 | 52.2 | 14.1 | 45.7 | 12.0 |
| 1 day | — | — | 19.0 | 7.49 | 45.0 | 6.07 | 23.2 | 6.75 |
| 3 days | — | — | 7.47 | 3.45 | 21.4 | 2.73 | 9.60 | 1.58 |
| 7 days | — | — | 5.24 | 1.72 | 11.9 | 2.86 | 7.20 | 1.79 |
| 10 days | — | — | 10.8 | 2.89 | 8.18 | 2.83 | 8.20 | 3.80 |
| 14 days | — | — | 15.1 | 5.01 | 4.35 | 1.67 | 4.58 | 1.88 |
| 21 days | — | — | 4.73 | 4.15 | — | — | 1.26 | 0.72 |
| 28 days | — | — | 1.47 | 1.77 | — | — | — | — |

Figure 4:
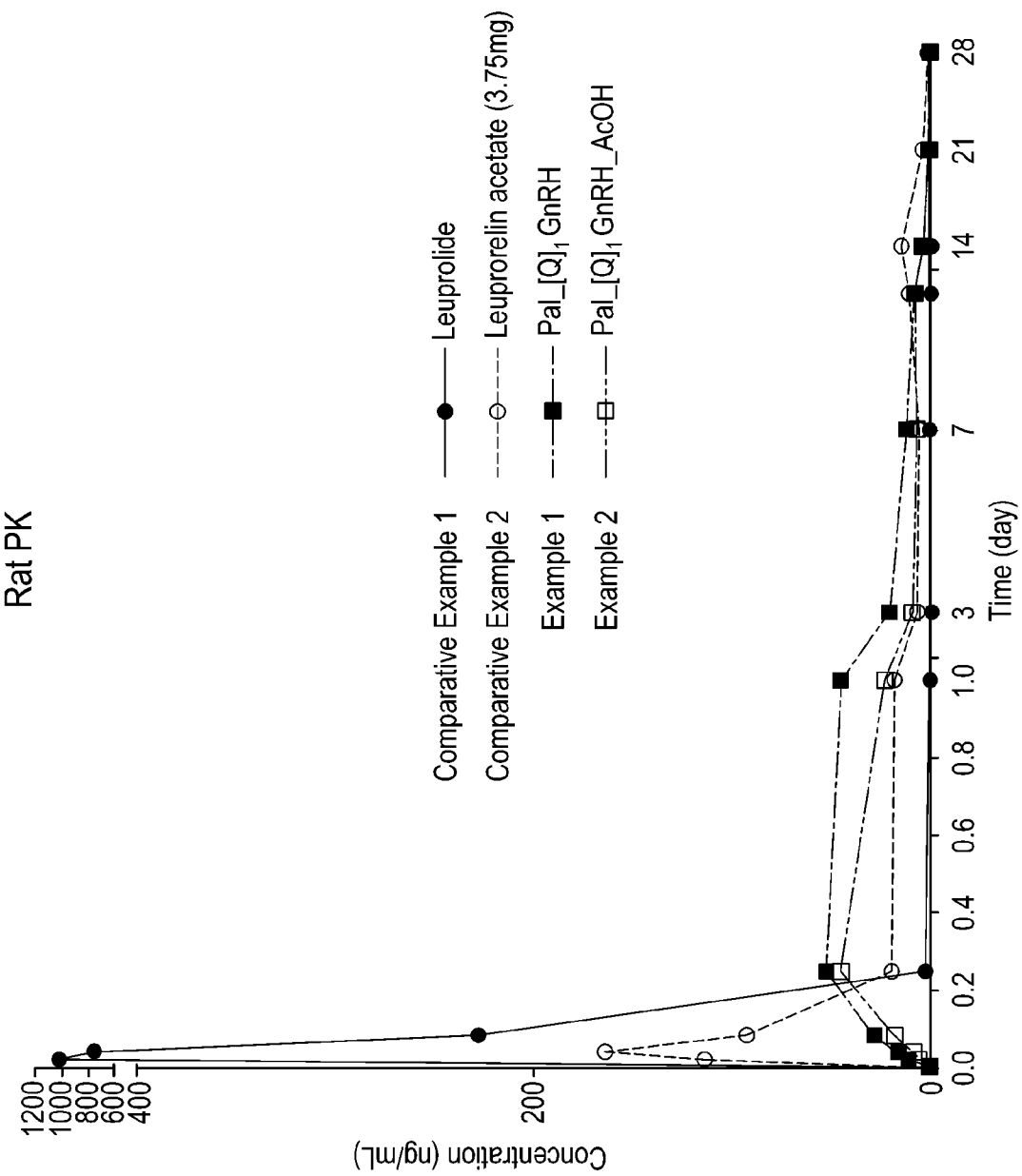
FIG. 4 is a graph showing the increased in vivo half-life of the palmitic acid-conjugated GnRH derivatives, where the blood concentration is plotted over time after the control drugs and the GnRH derivatives of the present disclosure are each subcutaneously administered once at a dose of 12.5 mg/kg to animals (rats).
Figure 5:
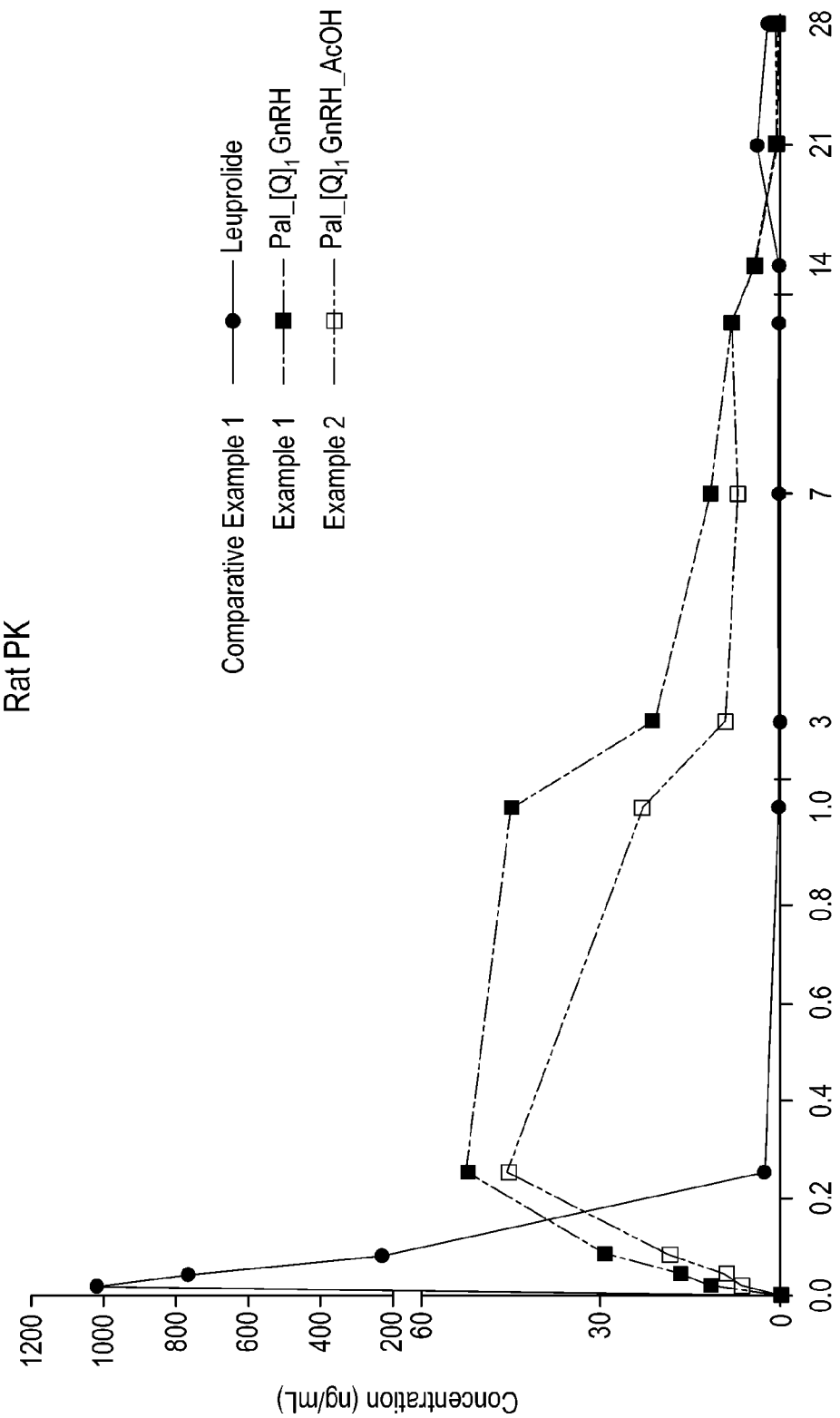
FIG. 5 is a graph showing the increased in vivo half-life of the palmitic acid-conjugated GnRH derivatives, where the blood concentration is plotted over time after the control drug of Leuprolide and the GnRH derivatives of the present disclosure are each subcutaneously administered once at a dose of 12.5 mg/kg to animals (rats).
Figure 6:
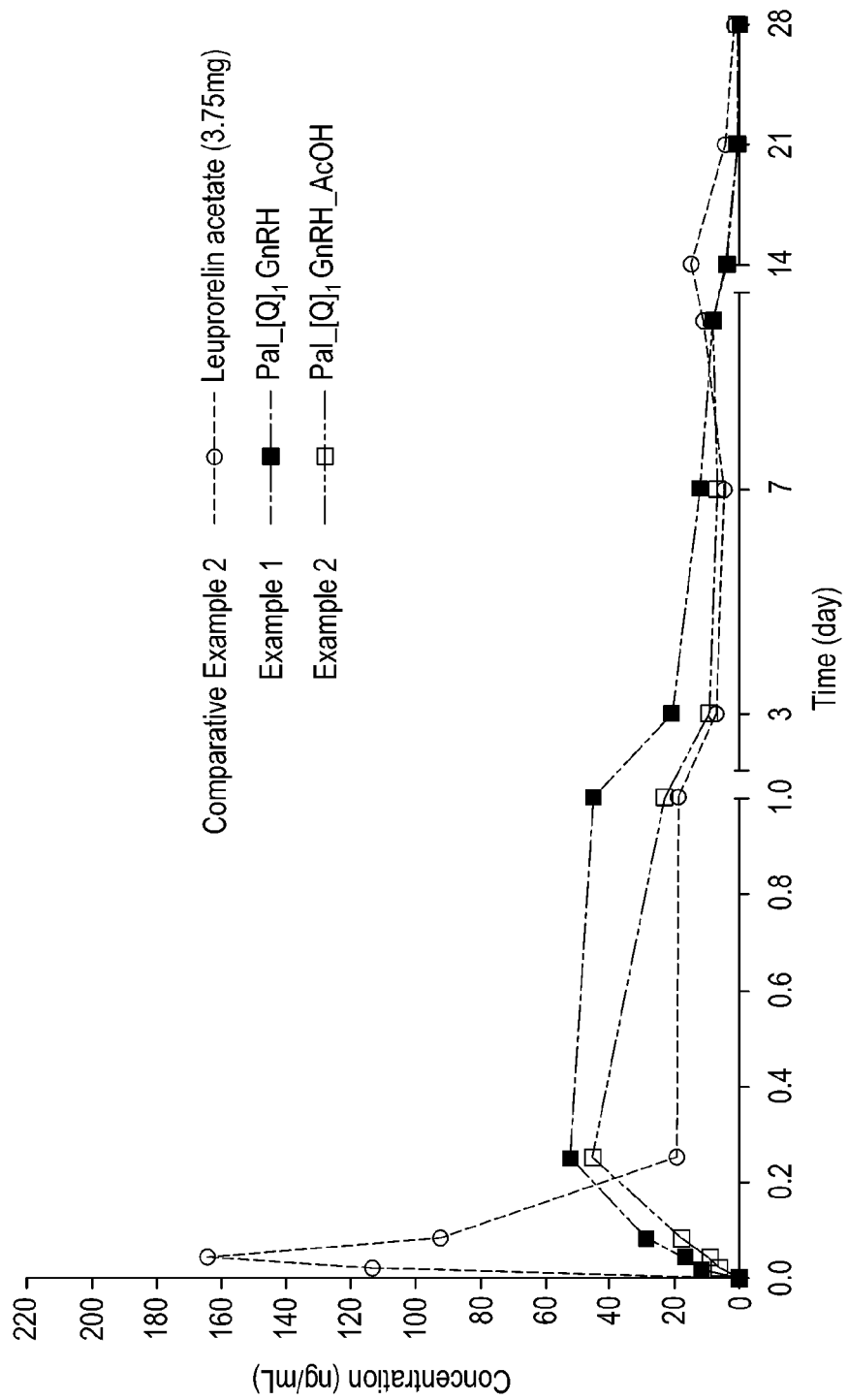
FIG. 6 is a graph showing the increased in vivo half-life of the palmitic acid-conjugated GnRH derivatives, where the blood concentration is plotted over time after the control drug of Leuprolide acetate depot one-month formulation and the GnRH derivatives of the present disclosure are each subcutaneously administered once at a dose of 12.5 mg/kg to animals (rats).

The measurement results are graphically depicted in FIGS. 4 to 6. Based on the results, pharmacokinetic analysis was carried out by calculating the half-life ($t_{1/2}$), clearance rate (CL), volume of distribution (Vd), time to reach the maximum concentration following drug administration ($T_{max}$), maximum concentration following drug administration ($C_{max}$), and systemic exposure to drug ($AUC_t$). The analysis results are as follows.

TABLE 7

| | Leuprolide | Leuprolide acetate (3.75 mg) | P2 Pal_[Q1]GnRH | P4 Pal_[Q1]GnRH AcOH |
|---|---|---|---|---|
| $t_{1/2}$ [day] | 0.03 | 4.17 | 4.80 | 4.03 |
| CL[(mg/kg)/(ng/ml)/day] | 0.180 | 0.049 | 0.051 | 0.075 |
| Vd[(mg/kg)/(ng/ml)] | 0.007 | 0.296 | 0.351 | 0.436 |
| $T_{max}$ [day] | 0.02 | 0.04 | 0.25 | 0.25 |
| $C_{max}$ [ng/ml] | 1020.0 | 164.0 | 52.2 | 45.7 |
| $AUC_t$ [ng/ml*d] | 69.21 | 245.22 | 216.24 | 159.51 |

As can be understood from the data, the palmitic acid-conjugated GnRH derivatives of the present disclosure are significantly superior to Leuprolide in terms of the in vivo half-life, clearance rate, volume of distribution, and systemic exposure ($AUC_t$). Further, the palmitic acid-conjugated GnRH derivatives of the present disclosure were found to have similar levels of half-life, clearance rate, and systemic exposure ($AUC_t$) to those of the commercially available Leuprolide formulation for one-month administration containing a biodegradable polymer and particularly to exhibit a superior volume of distribution, a delayed time to reach the maximum concentration following drug administration, and a reduced maximum concentration for a prolonged period of time, compared to the commercially available product. Taken together, the data demonstrate that the palmitic acid-conjugated GnRH derivatives of the present disclosure allow GnRH to maintain its suitable concentrations for a prolonged period of time in vivo.

In light of the excellent properties thereof, the palmitic acid-conjugated GnRH derivatives of the present disclosure can be used at a remarkably reduced volume, compared to the existing products comprising a biodegradable polymer for sustained release, and thus can overcome the disadvantage of pain and exclude the side effect that the biodegradable polymer remains in vivo for a long period of time. These properties are advantageous particularly to children. Meanwhile, when the palmitic acid-conjugated GnRH derivatives of the present disclosure were used in combination with the biodegradable polymer used in the conventional products, the half-life is remarkably increased, compared to conventional drugs such as Leuprolide, to become as long as drugs used in invasive methods (surgery), such as for implants (several months to one year).

Although the technical idea of the present disclosure has been described by the examples described in some embodiments and illustrated in the accompanying drawings, it should be noted that various substitutions, modifications, and changes can be made without departing from the scope of the present disclosure which can be understood by those skilled in the art to which the present disclosure pertains. In addition, it should be noted that that such substitutions, modifications and changes are intended to fall within the scope of the appended claims.

What is claimed is:

1. A long-acting palmitic acid-conjugated gonadotropin-releasing hormone (GnRH) derivative selected from the group consisting of,
   i) a sodium salt of the GnRH derivative comprising an amino acid sequence of SEQ ID NO: 4,
   ii) an acetate salt of the GnRH derivative comprising an amino acid sequence of SEQ ID NO: 5, and
   iii) an acetate salt of the GnRH derivative comprising an amino acid sequence of SEQ ID NO: 6, wherein a carboxyl group of the palmitic acid of the GnRH derivative is conjugated through a peptide-bond to an amino terminal of the peptide portion of the GnRH derivative.

2. The long-acting palmitic acid-conjugated GnRH derivative of claim 1, wherein the long-acting palmitic acid-conjugated GnRH derivative comprises the amino acid sequence of SEQ ID NO: 4.

3. The long-acting palmitic acid-conjugated GnRH derivative of claim 1, wherein the long-acting palmitic acid-conjugated GnRH derivative comprises the amino acid sequence of SEQ ID NO: 5.

4. A pharmaceutical composition for treatment of sex hormone-dependent disease, comprising the long-acting palmitic acid-conjugated GnRH derivative of claim 1, wherein the sex hormone-dependent disease is selected from the group consisting of prostate cancer, breast cancer, endometriosis, and central precocious puberty.

5. The pharmaceutical composition of claim 4, further comprising a biodegradable polymer selected from PLA (poly-lactic acid), linear or branched PLGA (poly(lactic-co-glycolic acid)), PGA (poly-glycolic acid), and hydrogel.

\* \* \* \* \*